US011273324B2

(12) United States Patent
Rantala

(10) Patent No.: US 11,273,324 B2
(45) Date of Patent: Mar. 15, 2022

(54) LED STRUCTURE AND LUMINAIRE FOR CONTINUOUS DISINFECTION

(71) Applicant: Illumipure Corp, Houston, TX (US)

(72) Inventor: Juha Rantala, Bäch (CH)

(73) Assignee: illumiPure Corp, Houston, TX (US)

( * ) Notice: Subject to any disclaimer, the term of this patent is extended or adjusted under 35 U.S.C. 154(b) by 0 days.

(21) Appl. No.: 15/871,171

(22) Filed: Jan. 15, 2018

(65) Prior Publication Data

US 2018/0147417 A1 May 31, 2018

Related U.S. Application Data

(63) Continuation-in-part of application No. 14/798,496, filed on Jul. 14, 2015, now abandoned.

(30) Foreign Application Priority Data

Jan. 13, 2017 (FI) .................................. 20175027

(51) Int. Cl.
*A61L 2/10* (2006.01)
*A61N 5/06* (2006.01)
(Continued)

(52) U.S. Cl.
CPC ............ *A61N 5/0624* (2013.01); *A61L 2/084* (2013.01); *A61L 2/10* (2013.01); *A61L 9/20* (2013.01); *H01L 25/0753* (2013.01); *H01L 33/08* (2013.01); *A61L 2202/11* (2013.01); *A61L 2202/25* (2013.01); *A61L 2209/12* (2013.01);
(Continued)

(58) Field of Classification Search
None
See application file for complete search history.

(56) References Cited

U.S. PATENT DOCUMENTS 3,670,193 A 6/1972 Thorington et al.
3,992,646 A 11/1976 Corth
(Continued)

FOREIGN PATENT DOCUMENTS

CN 104056289 9/2014
EP 2554583 2/2013
(Continued)

OTHER PUBLICATIONS

Neumark et al., "Wide Bandgap Light Emitting Materials and Devices", John Wiley & Sons, 2008 (Year: 2008).*
(Continued)

*Primary Examiner* — James Choi
(74) *Attorney, Agent, or Firm* — Lewis & Reese, PLLC

(57) ABSTRACT

A LED structure, a lighting fixture and a method of providing white light illumination. The LED structure comprises a substrate; a light emitting area defined on the substrate as a cavity; a first type of light emitting semiconductor source with bactericidal characteristics mounted in the cavity; a second type of light emitting semiconductor source mounted in the cavity with ability to excite the wavelength conversion material to generate white light; and a wavelength conversion material layer formed on top of the light emitting semiconductor sources. The invention enables disinfection by a lighting source or a luminaire visibly apparent to human as a white light source that is neither harmful to a human nor creates discomfort.

14 Claims, 6 Drawing Sheets

(51) Int. Cl.
| | | |
|---|---|---|
| *H01L 33/08* | (2010.01) | |
| *A61L 9/20* | (2006.01) | |
| *A61L 2/08* | (2006.01) | |
| *H01L 25/075* | (2006.01) | |
| *H01L 33/50* | (2010.01) | |

(52) U.S. Cl.
CPC .............. *A61N 2005/0652* (2013.01); *A61N 2005/0662* (2013.01); *A61N 2005/0663* (2013.01); *H01L 33/504* (2013.01)

(56) References Cited

U.S. PATENT DOCUMENTS

| | | |
|---|---|---|
| 6,242,752 B1 | 6/2001 | Soma et al. |
| 6,791,259 B1 | 9/2004 | Stokes et al. |
| 7,658,891 B1 | 2/2010 | Barnes |
| 8,398,264 B2 | 3/2013 | Anderson et al. |
| 8,476,844 B2 | 7/2013 | Hancock et al. |
| 8,508,204 B2 | 8/2013 | Deurenberg et al. |
| 9,039,966 B2 | 5/2015 | Anderson et al. |
| 9,046,227 B2 | 6/2015 | Aurelien |
| 9,333,274 B2 | 5/2016 | Peterson |
| 9,368,695 B2 | 6/2016 | Aurelien |
| 9,439,989 B2 | 9/2016 | Lalicki |
| 9,581,310 B2 | 2/2017 | Wu et al. |
| 2003/0124023 A1 | 7/2003 | Burgess et al. |
| 2004/0008523 A1 | 1/2004 | Butler |
| 2005/0055070 A1 | 3/2005 | Jones et al. |
| 2005/0207159 A1 | 9/2005 | Maxik |
| 2006/0022582 A1 | 2/2006 | Radkov |
| 2006/0071589 A1 | 4/2006 | Radkov |
| 2006/0186377 A1 | 8/2006 | Takahashi et al. |
| 2006/0262545 A1 | 11/2006 | Piepgras et al. |
| 2006/0284199 A1* | 12/2006 | Matheson ............... F21V 15/01 257/98 |
| 2008/0008620 A1 | 1/2008 | Alexiadis |
| 2008/0245788 A1* | 10/2008 | Choong ................ F24C 15/008 219/758 |
| 2008/0278927 A1 | 11/2008 | Li et al. |
| 2008/0305004 A1 | 12/2008 | Anderson et al. |
| 2008/0315217 A1 | 12/2008 | Van Der Wel |
| 2009/0018621 A1 | 1/2009 | Vogler et al. |
| 2009/0034236 A1 | 2/2009 | Reuben |
| 2009/0231832 A1 | 9/2009 | Zukauskas et al. |
| 2009/0267484 A1 | 10/2009 | Kasakura et al. |
| 2010/0001648 A1 | 1/2010 | De Clercq et al. |
| 2010/0121420 A1 | 5/2010 | Fiset et al. |
| 2010/0232135 A1 | 9/2010 | Munehiro et al. |
| 2010/0246169 A1 | 9/2010 | Anderson et al. |
| 2012/0099303 A1* | 4/2012 | Li ....................... H01L 25/0753 362/231 |
| 2012/0281408 A1 | 11/2012 | Owen et al. |
| 2012/0286304 A1* | 11/2012 | LeToquin .............. H01L 33/504 257/89 |
| 2012/0320607 A1 | 12/2012 | Kinomoto et al. |
| 2013/0077299 A1 | 3/2013 | Hussell et al. |
| 2013/0313516 A1 | 11/2013 | David et al. |
| 2013/0313546 A1 | 11/2013 | Yu |
| 2013/0320299 A1* | 12/2013 | Li ........................... H01L 33/06 257/13 |
| 2014/0254131 A1 | 9/2014 | Osinski et al. |
| 2014/0328046 A1 | 11/2014 | Aanegola et al. |
| 2015/0014715 A1* | 1/2015 | Hsing Chen ........ H01L 25/0753 257/89 |
| 2015/0049459 A1* | 2/2015 | Peeters ............... H01L 25/0753 362/84 |
| 2015/0129781 A1 | 5/2015 | Kretschmann |
| 2015/0182646 A1 | 7/2015 | Anderson et al. |
| 2016/0015840 A1 | 1/2016 | Gordon |
| 2016/0030610 A1 | 2/2016 | Peterson et al. |
| 2016/0249810 A1 | 9/2016 | Darty et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2021/0317981 A1* | 10/2021 | Higgins ................ F21V 23/003 |

FOREIGN PATENT DOCUMENTS

| | | |
|---|---|---|
| JP | 2003339845 | 12/2003 |
| WO | 2001/014012 | 3/2001 |
| WO | 2003/063902 | 8/2003 |
| WO | 2004/033028 | 4/2004 |
| WO | 2006/100303 | 9/2006 |
| WO | 2006/126482 | 11/2006 |
| WO | 2007/012875 | 2/2007 |
| WO | 2007/049180 | 5/2007 |
| WO | 2009/056838 | 5/2009 |
| WO | 2015/066099 | 5/2015 |
| WO | 2016/019029 | 2/2016 |

OTHER PUBLICATIONS https://www.digikey.com/en/articles/breakthrough-leds-reduce-size-and-cost-of-lighting-systems (Year: 2015).*

Dai, Tianhong, et al., "Blue Light for Infectious Diseases: Propionibacterium Acnes, Helicobacter Pylori, and Beyond?" National Institutes of Health—Drug Resist Update, Aug. 2012, 15(4), pp. 223-236.

Daicho, Hisayoshi, et al., "A Novel Phosphor for Glareless White Light-Emitting Diodes," Nature Communications, 3:1132, Oct. 16, 2012, 8 pages.

Neumark et al., "Wide Bandgap Light Emitting Materials and Devices," John Wiley & Sons, 2008.

Pinter, Matt, et al., "IEC/EN 62471 for LED Lighting Products—Standards for Eye and Skin Safety," Smart Vision Lights, 2009, 4 pages.

Setlur, Anant A., "Phosphors for LED-based Solid-State Lighting," The Electrochemical Society Interface, Winter 2009, 5 pages.

TRI-R Project Brochure, Toshiba Materials Co., Ltd., retrieved on Aug. 18, 2017, 16 pages.

* cited by examiner

LED STRUCTURE AND LUMINAIRE FOR CONTINUOUS DISINFECTION

FIELD OF INVENTION

The present invention relates to artificial lighting arrangements and methods used for disinfection by light. In particular, the present invention relates to the field of optoelectronics and white light emitting diodes (LEDs) providing bactericidal effects. The present invention relates to the applications of an integrated LED structure and continuously operating disinfection luminaire.

BACKGROUND ART

It is well known that ultra-violet (UV) sources have bactericidal and fungicidal effects, well suited for disinfection. Deep UV (UVC) sources are known to effectively prevent bacterial growth on surfaces and are widely used as germicidal sources. However, the drawback of usage of UVC sources such as Mercury lamps is the fact that UVC light is harmful for humans and thus prevents its use in presence of people. The mechanism behind the deep UV disinfection is known to be the cracking of DNA molecules, which have particularly strong absorption between 260-290 nm.

It is also known that longer wavelengths produce also bactericidal effects, although based on different physical mechanism. UVA light at 365 nm is known to inhibit bacterial growth and also blue/violet light produces similar growth blocking effects. Although the bactericidal effect is less strong at blue/violet wavelengths it can be exploited in continuously operating disinfection lights. The 405 nm light is well known to cause reactive oxygen species (ROS) generation in cells. These negatively charged oxygen ions in turn prevent cell metabolism and effectively suppress e.g. growth of bacterial colonies. While the intensity of the disinfection light is of primary importance, it is the total dose, expressed in terms of $J/m^2$, accumulated on the surface or on the objects, which ultimately define the disinfection power.

Any lower intensity source with suitable emission spectrum can be used for disinfection as long as the exposure times are long enough but still of practical value. However, again the human presence sets boundaries for such lights. International regulations and safety guidelines are defined by the International Commission on Non-Ionizing Radiation Protection (ICNIRP) and IEC standard IEC-62471. Again, the ICNIRP defines ultra-violet wavelengths to be 100-400 nm.

If the radiation source has a short wavelength emission, say below 410 nm, and this short wavelength emission is the dominating intensity or color, humans are commonly experiencing discomfort.

Known growth lights for plant growth and photosynthesis comprise blue and red light sources that are sometimes accompanied with white light sources. Hence they are not addressing issues relating to antibacterial and fungicidal function.

A light source applying LEDs and UV germicidal lamp is disclosed in CN 104056289 A. However, again such assembly is not suitable for general lighting due to detrimental effects of UV light to humans.

A LED source with disinfection capability in closed environment is presented in EP 2554583 A1. Again such source emitting wavelengths below 300 nm is not suitable for general lighting due to detrimental effects of UV light to humans.

According to our laboratory tests a combination of individual, spatially separated LEDs with 405 nm emission and individual white light LEDs results in a light source that causes discomfort. A light source based on individually packaged LEDs does not produce a smooth and uniform light field. Particularly point sources with intensive short wavelength emission are disturbing. It is necessary to provide a source in which the short wavelength point sources are not distinctively visually appearing between the white light LEDs. However, physical overlaying of the white light LEDs with 405 nm LEDs is not straightforward or possible.

An example of spatially mixing the source is shown in US8398264. A diffuser plate is used in conjunction with Fresnel type lens to provide uniform emissions and to avoid direct visibility of individual short wavelength emitters in the source plane. The known diffuser based constellation is complex and expensive.

SUMMARY OF INVENTION

To solve above discussed problems it is an object of the present invention to provide a method of white light illumination using an integrated light emitting diode structure with an adjustable emission spectrum with disinfection capability.

It is an aspect of certain embodiments to provide an integrated LED structure functioning as a white light source and comprising; a substrate, at least one or a plurality of emission areas, and an electrical two or three wire control interface.

It is another objective to prevent the discomfort perceived by humans from radiation source having a short wavelength emission, which is the dominating intensity or color.

The present invention is based on the concept of providing a LED structure comprised of
  a substrate;
  a light emitting area defined on the substrate as a cavity;
  a first type of light emitting semiconductor source with bactericidal and germicidal characteristics mounted in the cavity; and
  a second type of light emitting semiconductor source mounted in the cavity with ability to excite the wavelength conversion material to generate white light.

In another embodiment, the LED structure is comprised of a substrate,
  a light emitting area defined on the substrate as a cavity,
  a light emitting semiconductor source mounted in the cavity,
  a wavelength conversion material layer formed on the top of the light emitting semiconductor source, and
  an electrical circuit layer, optionally on the top surface of the substrate, for connecting the said light emitting semiconductor source to electrical control interface.

In another embodiment, the LED structure is comprised of a substrate,
  a light emitting area defined on the substrate as a cavity,
  a light emitting semiconductor source mounted in the cavity,
  a wavelength conversion material layer formed on the top of the light emitting, semiconductor source, and
  an electrical circuit layer for connecting the said light emitting semiconductor source to electrical control interface, the light emitting semiconductor source has a peak wavelength emission above ultraviolet wavelengths and below 410 nm, preferably substantially at 405 nm, and the full width half maximum of the emission is below 30 nm.

Typically, there is wavelength conversion material layer formed on top of the light emitting semiconductor sources, and an electrical circuit layer for connecting the light emitting semiconductor sources to electrical control interface.

The present invention also provides a lighting fixture facilitating white light illumination and continuous disinfection functionality comprising at least one integrated LED source having a first emission, which is non-perceptible to human eye, in the range of 360 to 430 nm and a full width half maximum of less than 30 nm, and a second emission peak, which is perceptible to human eye as a white light, with maximum emission in the range of 430 to 700 nm. In preferred embodiments the emitters are of two different types and have emission peaks near or at wavelength of 405 nm and near or at wavelength of 450 nm.

More specifically the present invention is characterized by what is stated in the characterizing parts of the independent claims.

Considerable advantages are obtained.

Thus, the present invention provides an integrated LED structure and a luminaire which achieve a continuous disinfection process.

The invention enables disinfection by a lighting source or a luminaire visibly apparent to human as a white light source that is neither harmful to humans nor creates discomfort. This aim is achieved by overlaying the short wavelength emission with white light emission. Such a white light source or a luminaire is suitable for the general illumination purposes while simultaneously providing means to disinfect exposed surfaces and objects. The said emission area typically comprises one or several LED semiconductor diodes, which are technically reliable and economically viable, as light emitters to provide the light emission.

The use of electromagnetic radiation at wavelength of 405 nm as disclosed in this invention is safe. The new type of LED sources disclosed avoids the disturbing effect of the short wavelength visible light.

In specific embodiments, the invention also achieves a light source that provides for disinfection of an object and also simulated photosynthesis of plants. Thus, the present integrated LED structure can be incorporated into white light sources for providing disinfection with bactericidal and fungicidal, anti-viral (germicidal), and photosynthesis effects.

The present invention provides disinfection functionality for general lighting and photosynthesis lighting enabled by the disclosed integrated LED structure and luminaire.

Spatial integration gives an integrated LED structure which has both 405 nm emission source and a 450 nm blue emission source buried under a wavelength conversion layer, in very near vicinity of each other. In a preferred embodiment, independent control of the two emissions, namely the 405 nm radiation and the white light emission, are provided for. This allows for the control of intensity of 405 nm radiation so that in situations where no white light is necessarily needed, only 405 nm radiation can be used and with maximum intensity, while white light radiation can be turned off. And conversely when e.g. humans, or in some applications animals, are present the radiation intensity of 405 nm can be turned low, or completely off, while maintaining suitable level of white light illumination.

With the integrated LED structure the white light quality parameters, such as CRI and CCT, remain constant as the 405 nm emission has negligible contribution to the luminous flux or illuminance.

The integrated structure provides means for spatially mounting the emitter with bactericidal and germicidal effect in close vicinity of the white light source, and in some embodiment even to combine them. When the intensity of the bactericidal short wavelength is appropriately chosen with respect to the white light intensity, the source appears as a normal white light source to human eye. Furthermore the spatial arrangement guarantees that the emission of 405 nm is not distinguishable for humans due to overlaying white light emission.

BRIEF DESCRIPTION OF DRAWINGS

The invention will now be further described, by way of non-limiting examples, with reference to the accompanying diagrammatic drawings. In the drawings.

DESCRIPTION OF EMBODIMENTS

Figure 1:
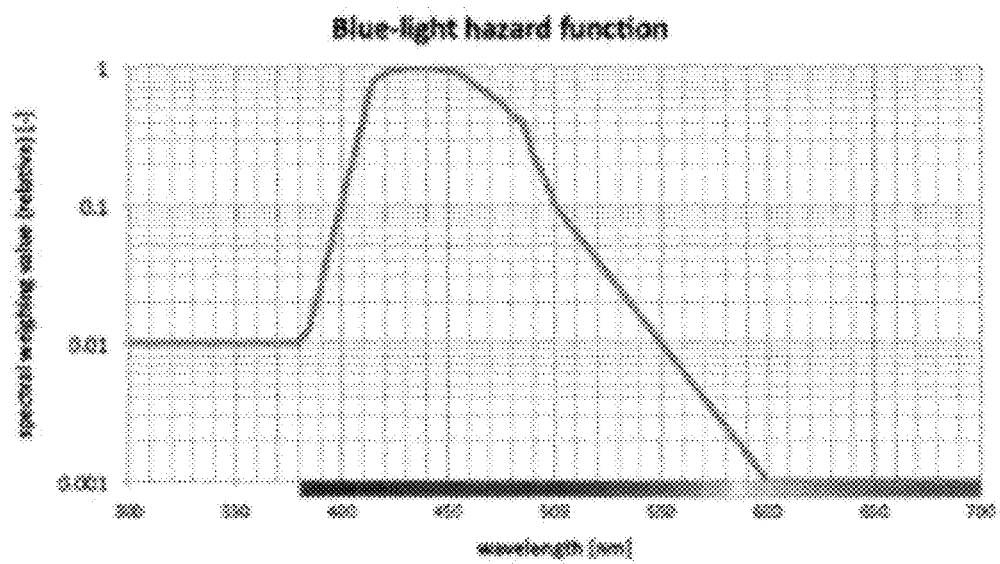
FIG. 1 is a graph presenting spectral weighting function of blue-hazard light
Figure 2:
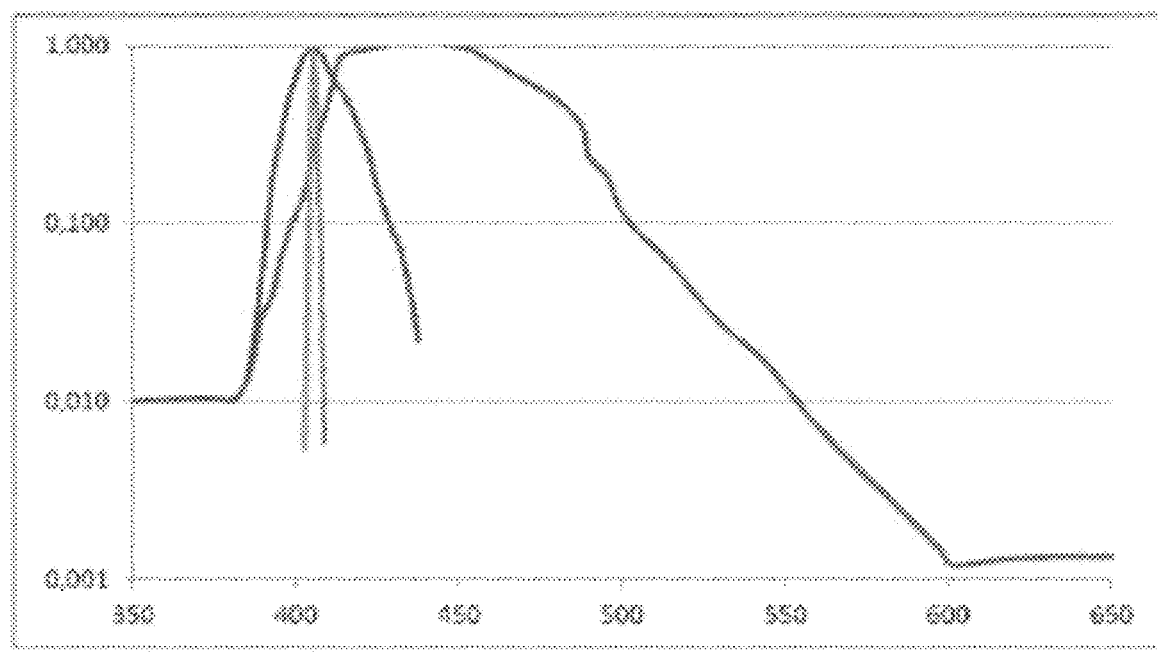
FIG. 2 is a graph presenting spectral weighting function of blue-hazard light with typical emission spectrum of light emitting diode at 405 nm and a typical emission spectrum of a laser diode at 405 nm.
Figure 3:
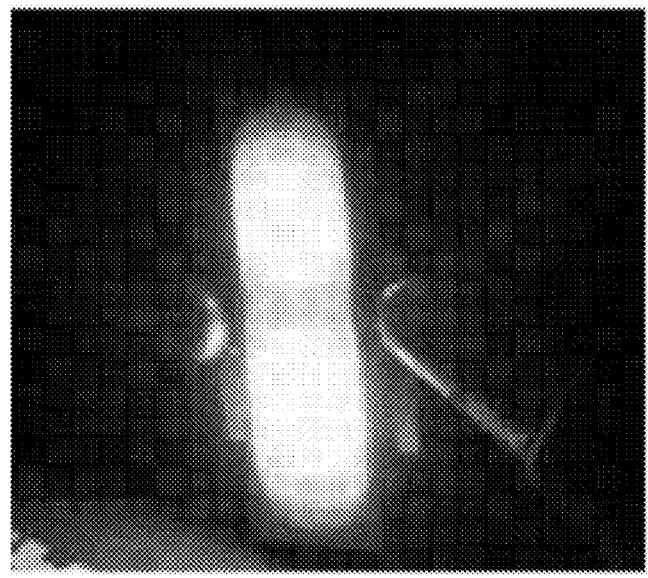
FIG. 3 is a photo of LED source for continuous disinfection luminaire with spatially combined white light emitter and low wavelength emitter in one LED source and the spectrum is spatially combined.

The following descriptions are merely non-limiting examples and it will be appreciated by one skilled in the art that specific details of the examples may be changed without departing from the spirit of the invention.

The present technology provides an integrated LED structure and a luminaire for enabling, for example, a continuous disinfection process.

In one embodiment, disinfection is achieved by a lighting source or a luminaire visibly apparent to human as a white light source that is firstly not harmful to a human and secondly is not creating discomfort. Such a white light source or a luminaire is suitable for the general illumination purposes while simultaneously providing means to disinfect exposed surfaces and objects.

The present technology also achieves a light source that provides for disinfection of objects and also simulated photosynthesis of plants. The disclosed integrated LED structure can be incorporated into white light source for providing disinfection with bactericidal and fungicidal, anti-viral (germicidal), anti-viral and photosynthesis effects.

Thus, disinfection functionality can be achieved for general lighting and photosynthesis lighting, enabled by the disclosed integrated LED structure and luminaire.

In an embodiment, the emission area comprises wavelength conversion material to provide means for white light emission. Emission area comprises in some preferred embodiment more than one type of wavelength conversion materials. The materials can be layered vertically upon each other, or horizontally with different materials adjacent to each other, or in mixed material layers, to achieve high efficiency or high color rendering index (CRI), or wanted color correction temperature (CCT).

The light emitters are in some cases electrically connected in series or parallel to enable a common current drive scheme. The control interface has then at least one wire for providing the common drive current and least one ground wire to close the current path back to power supply. However, in some cases the emitters are not connected electrically enabling independent intensity control. The control interface has then at least three wires for providing the drive current independently, and at least one ground wire to close the current path back to power supply.

In an embodiment, the integrated LED component or package has two different types of semiconductor emitters, which can be also in independent in terms of electrical circuits. In a nominal operation point the current is adjusted for both emitters are simultaneously, however, electrical circuitry being independent current is adjusted separately and the emission appears as white light in both cases, but with the emission spectrum having a spectroscopically observable double peak structure with blue emission at or near 450 nm and violet emission at or near 405 nm.

If the intensity of the 405 nm emission is A and the intensity of the 450 nm emission is B, the ratio A/B can be now freely adjusted with the two independent drive currents. In nominal situation the ratio is adjusted so that the emission of 405 nm is distinguishable for human and is within the safety limits as discussed earlier. The source is emitting white light and same time giving low intensity emission at 405 nm to provide continuous disinfection functionality.

In an embodiment, the intensity control is exploited dynamically depending of the human presence. In the first case of no human presence the ratio A/B can be maximized. In the second case of human presence the intensity A can be adjusted to a low value, and to comply with the safety standards. Thus there are at least two set points of operation in typical case. In the first set point of operation, the drive current is tuned up to e.g. 350 mA for the 405 nm emitter, while the drive current for the 450 nm emitter can be tuned down to 0 mA. In the second set point the drive current is tuned down to e.g. 50 mA for the 405 nm emitter, and the drive current for the 450 nm emitter is tuned to e.g. 350 mA. Thus while still maintaining the white light emission, the LED is providing illumination with bactericidal and germicidal effect. Such intensity tuning is beneficial for ensuring safety in presence of humans, and to avoid exposure to high intensity radiation at 405 nm.

In some preferred mode of use, the dynamic intensity tuning can be exploited to adjust the emission of 405 nm after a certain total radiation dose has accumulated on the target surface. This can be detected by integrating the specific wavelength signal with a detector circuit and providing the necessary feedback to control appropriately the output of the integrated LED structure. This is beneficial for reducing energy consumption and to lengthen the life time of the LED by avoiding unnecessary use of the 405 nm emitter.

The complete emission of the white light source is formed of as a sum of the emission of the 405 nm emitter and of the emission of the 450 nm emitter, and the emission from the wavelength conversion material, which is excited by the emission of the 450 nm emitter.

In some embodiments the integrated LED structure comprises only one type of light emitter, preferably having a short wavelength emission below wavelength of 410 nm, and a wavelength conversion material layer formed on top of the emitter.

In some preferred embodiments the complete white light source emission the light emission spectrum is formed of as a sum of emission from the 405 nm emitter and the emission from the wavelength conversion material, excited by the emission at 405 nm.

Preferably, the light emitter is capable of high intensity emission, whereby a wavelength conversion material layer formed on top of the light emitter capable of a peak emission of light above ultraviolet wavelengths and below 410 nm, preferably substantially at 405 nm, may be bleached by the high intensity emission.

In an embodiment, the wavelength conversion material layer may be adapted to have a low absorption at emission wavelengths above ultraviolet wavelengths and below 410 nm. Preferably the absorption is low at least at or close to emission wavelength of 405 nm. The absorption of the wavelength conversion material should be adapted to allow at least 10% of the emission of the semiconductor light source to be transmitted through the wavelength conversion material layer. In this way, a led structure may provide efficient disinfection at the low absorption wavelengths of the wavelength conversion material layer.

It should be appreciated that the adapted wavelength conversion material layer may support the high intensity emission causing bleaching of the wavelength conversion material layer.

In preferred embodiments the wavelength conversion material is a phosphor based e.g. in YAG:Ce materials providing white light emission spectrum with CRI and CCT characteristics suitable for general lighting applications. The wavelength conversion material has in this case a relatively low extinction coefficient at the wavelength range of 360 to 410 nm to avoid excessive absorption of the emission below 410 nm.

The said emission areas can be formed as buried shallow cavity on the top surface of the said substrate. In some preferred embodiments the LED structure can comprise several emission areas in buried cavities of different heights.

In some embodiments the short wavelength emitter has an emission wavelength that has bactericidal, germicidal or fungicidal effects. In preferred embodiments the short wavelength emission or intensity has no or negligible detrimental effects to human skin, human eyes, or human health in general.

In some embodiments the short wavelength emitter has an emission wavelength that has bactericidal, germicidal or fungicidal effects and the emitter is also emitting at wavelengths to support, enhance and propagate photosynthesis in plants.

As referred to above, in one further embodiment, the LED structure is comprised of a substrate, a light emitting area defined on the substrate as a cavity, a light emitting semiconductor source mounted in the cavity, a wavelength conversion material layer formed on the top of the light emitting semiconductor source, and an electrical circuit layer, optionally on the top surface of the substrate, for connecting the said light emitting semiconductor source to electrical control interface. Specific embodiments of this embodiment include the following:

LED structures, wherein the wavelength conversion material layer is adapted to have a low absorption, allowing at least 10% of the emitted light to be transmitted through the wavelength conversion material layer, at emission wavelengths above ultraviolet wavelengths and below 410 nm.

LED structures, wherein the wavelength conversion material layer is bleached by a high intensity emission of the light emitting semiconductor sources.

LED structures, comprising a second light emitting semiconductor source mounted in the cavity and having a peak wavelength emission substantially at 470 nm.

LED structures, wherein the light emitting semiconductor source has the peak light emission in the wavelength range of 365 to 410 nm, and the full width half maximum of the emission is below 30 nm;

LED structures, wherein the emission area comprises of a wavelength conversion material with a light emission band being in the wavelength range of 425 to 750 nm, with the peak emission being in the wavelength range of 450 to 650 nm and the full width half maximum of the emission is at least 50 nm;

LED structures, wherein there is only one type of light emitting semiconductor source, which has a peak light emission in the wavelength range of 365 to 430 nm, with a center emission located close to 405 nm, and the full width half maximum of the emission is below 30 nm;

LED structures, wherein the first type of light emitting semiconductor source has a peak light emission in the wavelength range of 365 to 430 nm, and the full width half maximum of the emission is below 30 nm and local emission peak of a wavelength conversion material in the wavelength range of 450 to 750 nm;

LED structures, wherein the first type of light emitting semiconductor source has a peak light emission in the wavelength range of 365 to 430 nm, and the full width half maximum of the emission is below 30 nm and third emission peak of a wavelength conversion material in the wavelength range of 450 to 750 nm; and LED structures, wherein CRI of visible spectrum is over 70 and the color temperature is between 2000 K and 8000 K and that at least 5% optical power is emitted between 365 nm and 430 nm wavelength range.

As referred to above, in one further embodiment a LED structure comprises a substrate, a light emitting area defined on the substrate as a cavity, at least two light emitting semiconductor sources with bactericidal and germicidal characteristics mounted in the cavity. Both of the light emitting semiconductor sources have ability to excite a wavelength conversion material to generate white light and at least one of the light emitting semiconductor sources have a peak wavelength emission above ultraviolet wavelengths and below 410 nm, preferably substantially at 405 nm, and the full width half maximum of the emission is below 30 nm. A wavelength conversion material layer is formed on top of the light emitting semiconductor sources to be excited by the light emitting semiconductor sources. Specific embodiments of this embodiment include the following:

LED structures comprising, wherein the wavelength conversion material layer is adapted to have a low absorption, allowing at least 10% of the emitted light to be transmitted through the wavelength conversion material layer, at emission wavelengths above ultraviolet wavelengths and below 410 nm;

LED structures comprising, wherein the wavelength conversion material layer is bleached by a high intensity emission of the light emitting semiconductor sources; and LED structures comprising a second light emitting semiconductor source mounted in the cavity and having a peak wavelength emission substantially at 470 nm.

In an embodiment, one or more LED structures may be comprised in lighting fixtures to provide a method, the method comprising:

in the presence of humans, the light source is adjusted to provide white light illumination with a bactericidal and optionally germicidal low-intensity emission in the background of the white light emission, non-perceptible to human eye; and in a situation with no humans present, the white light illumination is turned off, while the bactericidal and optionally germicidal emission is maximized.

Figure 4:
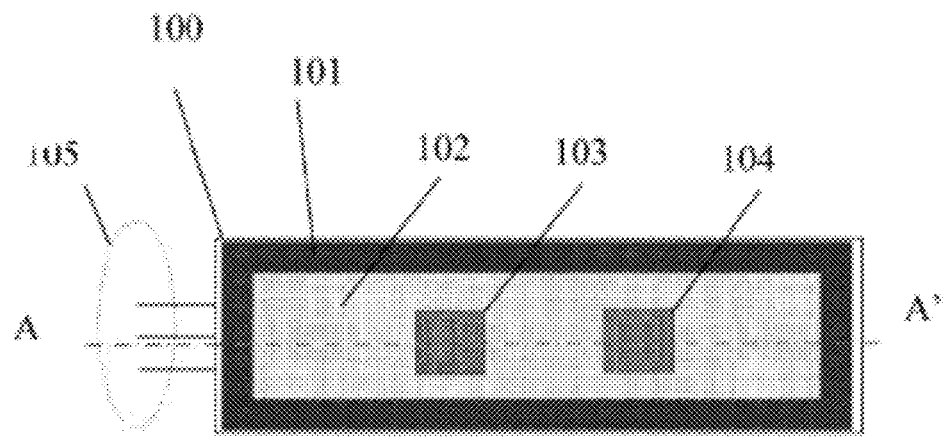
FIG. 4 is a schematic top side view of an integrated LED structure according to an embodiment of the present invention.
Figure 5:
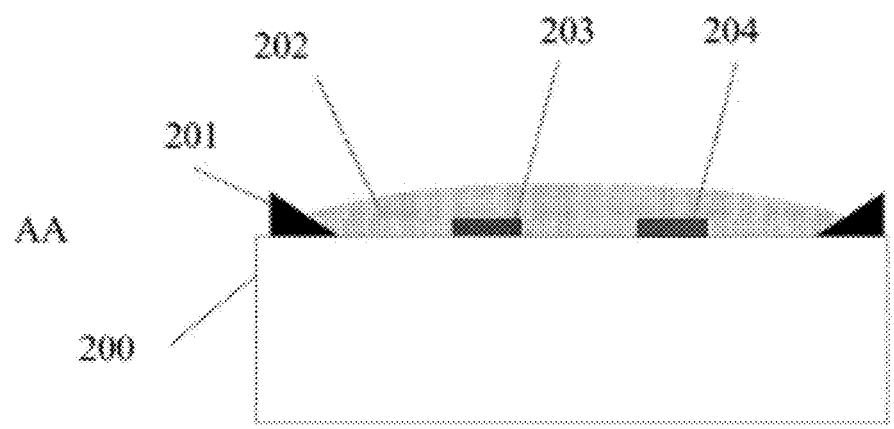
FIG. 5 is a schematic view of the cross-section of an integrated LED structure according to an embodiment of the present invention.

Turning now to the embodiments shown in the drawings, and specifically to FIG. 4, it can be noted that in one embodiment (yellow phosphor), the LED structure is comprised of a substrate 100, an emission area inside the cavity wall 101, wavelength conversion material layer 102, an emitter with main emission centered around 405 nm wavelength 103, an emitter with main emission centered around 450 nm wavelength 104, and a three wire control interface 105.

The emission area comprises the first type of LED semiconductor chip 203 emitting at between 385 nm and 430 nm, and having a full width half maximum (FWHM) emission of 5 to 20 nm. The emission area comprises also a second type of LED semiconductor chip 204 emitting at between 430 nm and 500 nm, and wavelength conversion material 202 having its peak emission at between 500 nm and 700 nm and having a full width half maximum emission of about 100 nm.

The control interface is having a three wire structure and is to enable independent control of the said two semiconductor chips.

Figure 6:
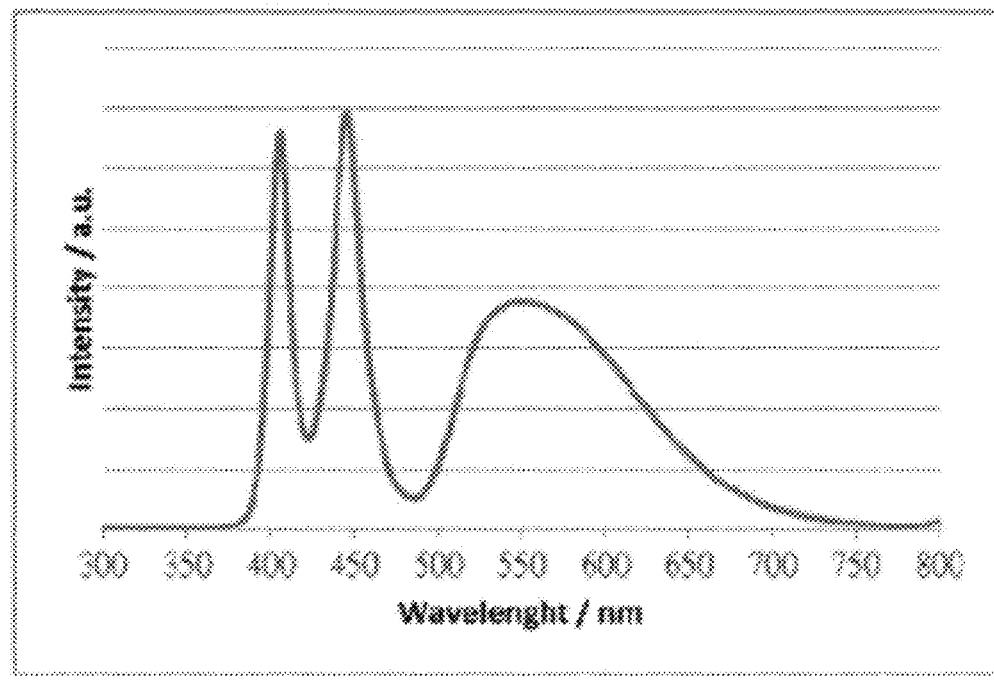
FIG. 6 is a graph representing a typical emission spectrum of an integrated LED structure according to an embodiment of the present invention.
Figure 7:
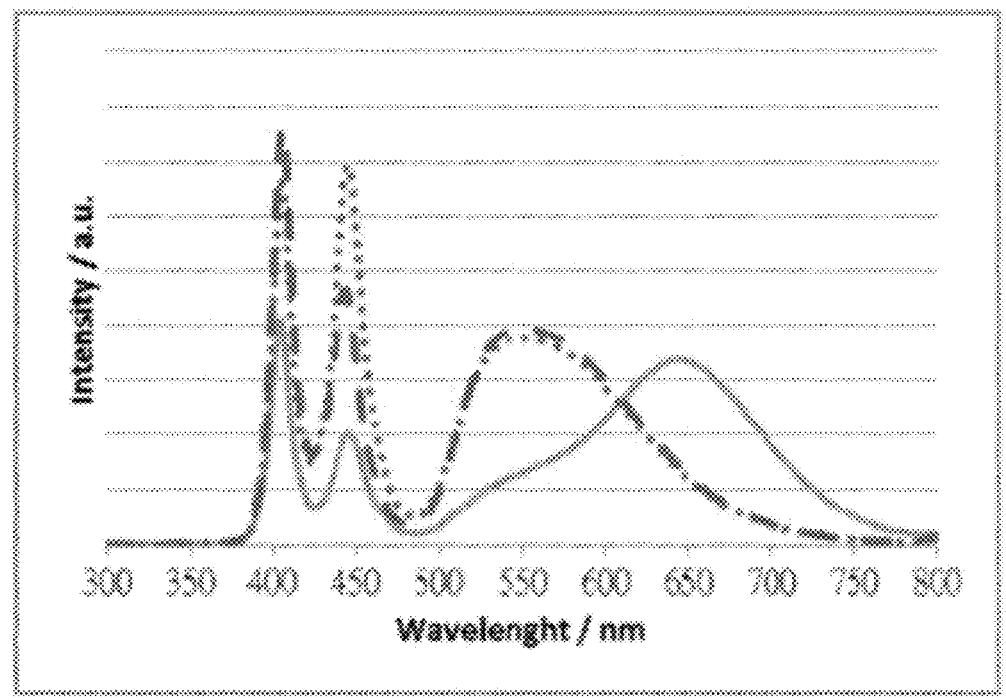
FIG. 7 is a graph representing a typical emission spectrum of an integrated LED structure according to an embodiment of the present invention.

The LED structure emits a spectrum as shown in FIG. 6. By controlling the current of the first semiconductor chip emitting at 405 nm, the spectrum can be tuned dynamically as shown in the FIG. 7 (dotted and dashed lines). Or by changing the wavelength conversion material as shown in the FIG. 7 (solid line).

Figure 8:
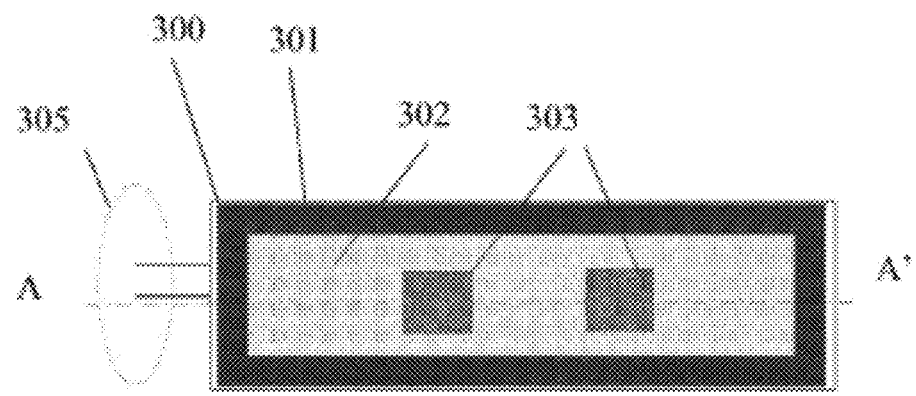
FIG. 8 is a schematic top side view of an integrated LED structure according to an embodiment of the present invention.

In another embodiment (UV phosphor), and referring specifically to FIG. 8, the LED structure is comprised of a substrate 300, an emission area inside the cavity wall 301, wavelength conversion material 302, two emitters with main emission centered around 365 and 430 nm wavelength 303, and a two wire control interface 305.

The emission area comprises a single type of LED semiconductor chips 403 emitting at 405 nm, and having a full width half maximum (FWHM) emission of about 14 nm. The emission area also comprises of wavelength conversion material layer 402 having its relatively high extinction coefficient at 405 nm and peak emission between 500 to 700 nm and having a full width half maximum (FWHM) emission is normally more than 30 nm.

The control interface is having a two wire structure and is to enable electrical control of the said emitter chips.

Figure 10:
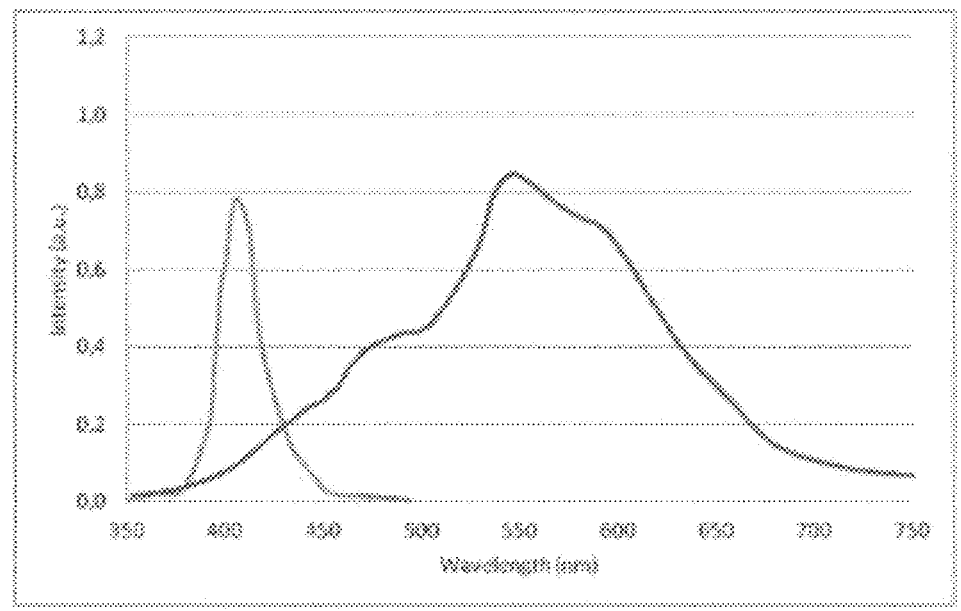
FIG. 10 is a graph representing a typical emission spectrum of an integrated LED structure according to an embodiment of the present invention.

The LED structure emits a spectrum as shown in FIG. 10.

Figure 9:
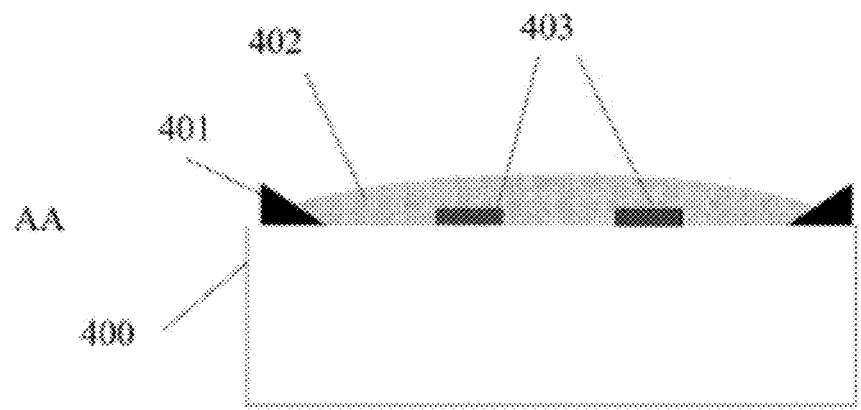
FIG. 9 is a schematic view of the cross-section of an integrated LED structure according to an embodiment of the present invention.

Another set of tests with spatially combined LEDs with 405 nm emission fully embedded in the white light emission, in standard Surface Mount Device (SMD) of 5630 package type, were carried out. Schematic representation of this embodiment is shown in FIGS. 8 and 9.

Two GaN semiconductor chips emitting light with center emission at 405 nm wavelength were first mounted in the 5630 package and wire bonded. The chips were in close proximity of each other. The wavelength conversion layer was next dispensed over these two chips in to the cavity of the 5630 package. The thickness and the phosphor concentration of the wavelength conversion layer was varied in order to find optimum thickness and concentration. The five samples thus have slightly varying characteristics in terms of CRI, CCT and efficiency. As the 405 nm was fully embedded in the wavelength conversion layer it was not possible to visually distinguish the 405 nm emission from the white light emission.

Figure 11:
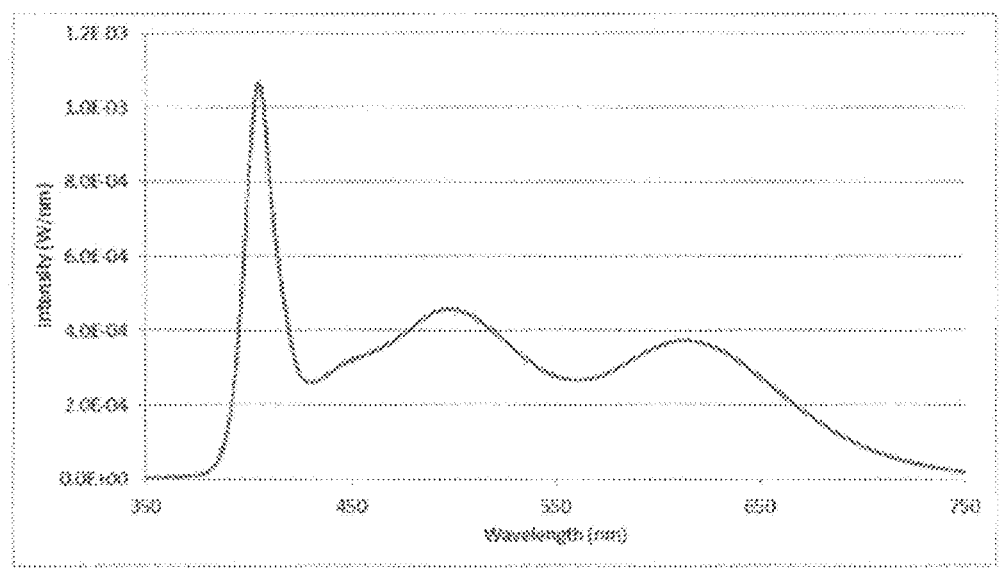
FIG. 11 is a graph representing a typical emission spectrum of an integrated LED structure according to a further embodiment of the present invention

The spectrum of the above structure is shown in FIG. 11. The solid curve in the figure depicts a typical measured spectrum of the sample LEDs.

The high transmission of 405 nm emission through the wavelength conversion layer was possible and was measured to be between 17 to 24 mW, while the total optical output was measured to be 116 to 126 mW. These sample units had an electrical to optical conversion efficiency of 33 to 36%. The CRI of the white light was 83 to 95 with CCT being 4954 to 6918 K.

The below table shows the measured test results of these LED samples.

TABLE

| Sample | Wavelength span (nm) | Vf (V) | P (mW) | Flux (lm) | Fe (mW) | Eff. (lm/W) | x | y | Tc (K) | Ld (nm) | Lp (nm) | HW (nm) | CRI | Eff %. (Fe/P) |
|---|---|---|---|---|---|---|---|---|---|---|---|---|---|---|
| 1 | 300-1000 | 3.12 | 351.20 | 24.68 | 123.80 | 70.3 | 0.332 | 0.334 | 5541 | 493.1 | 403.8 | 17.5 | 83 | 35 |
|   | 300-415 | 3.12 | 350.60 | NA | 23.12 | 0.0 | 0.173 | 0.005 | NA | 408.5 | 403.8 | 17.6 | NA | 7 |
| 2 | 300-1000 | 3.13 | 352.30 | 25.14 | 114.90 | 71.4 | 0.346 | 0.351 | 4954 | 574.3 | 403.5 | 18.0 | 87 | 33 |
|   | 300-415 | 3.12 | 351.20 | NA | 16.58 | 0.0 | 0.173 | 0.005 | NA | 408.5 | 403.5 | 18.0 | NA | 5 |
| 3 | 300-1000 | 3.13 | 351.80 | 23.96 | 121.20 | 68.1 | 0.320 | 0.344 | 6056 | 502.6 | 405.4 | 17.7 | 94 | 34 |
|   | 300-415 | 3.13 | 351.70 | NA | 22.74 | 0.0 | 0.173 | 0.005 | NA | 408.5 | 404.5 | 17.6 | NA | 6 |
| 4 | 300-1000 | 3.13 | 352.20 | 24.71 | 116.10 | 70.2 | 0.347 | 0.365 | 4974 | 568.6 | 403.7 | 17.4 | 94 | 33 |
|   | 300-415 | 3.18 | 357.40 | NA | 17.45 | 0.0 | 0.173 | 0.005 | NA | 406.5 | 403.6 | 17.3 | NA | 5 |
| 5 | 300-1000 | 3.12 | 350.70 | 24.86 | 115.70 | 70.9 | 0.334 | 0.360 | 5444 | 555.7 | 405.7 | 18.5 | 95 | 33 |
|   | 300-415 | 3.12 | 350.40 | NA | 16.80 | 0.0 | 0.173 | 0.005 | NA | 408.5 | 405.6 | 17.5 | NA | 5 |
| 6 | 300-1000 | 3.14 | 353.20 | 25.37 | 126.40 | 71.9 | 0.302 | 0.344 | 6918 | 496.3 | 403.6 | 17.2 | 93 | 36 |
|   | 300-415 nm | 3.13 | 351.50 | NA | 23.84 | 0.0 | 0.173 | 0.005 | NA | 406.5 | 403.5 | 17.2 | NA | 7 |

The above-described embodiment has the additional benefit that the white light emission is without an emission peak at 450 nm. As is well known blue wavelengths are considered hazardous (blue hazard). With this embodiment safer white light illumination is provided.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

INDUSTRIAL APPLICABILITY

The disclosed integrated LED structure has applications for example but not limited to in food production and processing sites, airplanes and hospitals. The ability to have white light illumination and simultaneously having disinfection functionality can greatly reduce infection diseases. Particularly interesting applications are refrigerators at domestic use. In such closed environments low-cost, energy efficient integrated LED structure can be applied in very efficient manner. While the refrigerator's door is closed the emission of short wavelength disinfection emission can be tuned to high intensity and white light can be turned off. Again during anyone opening the door the emission of the short wavelength can be turned off and the white light emission can be turned on.

Another application for continuous disinfection with white light is found with fruit, vegetable, fish and meat desks in grocery stores. Use of continuous disinfection white light in such places would reduce risks of spreading infections while improving the shelf life of fresh products.

In operating rooms in hospitals, as well as in patient rooms and airplanes white lights with disinfection functionality can be applied to reduce risk for infections.

Another use in greenhouses and food factories to provided photosynthesis (so call growth) for plants and simultaneously provide germicidal or fungicidal effects for the plants.

REFERENCE SIGNS LIST 100 substrate
101 cavity wall
102 wavelength conversion material layer
103, 104 emitter
105 control interface
200 substrate
201 cavity wall
202 wavelength conversion material layer
203, 204 semiconductor chip
300 substrate
301 cavity wall
302 wavelength conversion material layer
303 emitter
305 control interface
400 substrate
401 cavity wall
402 wavelength conversion material layer
403 semiconductor chip

CITATION LIST

Patent Literature

U.S. Pat. No. 8,398,264
CN 104056289 A
EP 2554583A1

Non-Patent Literature

IEC standard IEC-62471

The invention claimed is:
1. A method for providing illumination and disinfection using a light emitting structure,
the light emitting structure comprising:
a substrate comprising a cavity configured as a light emitting area;
a first light emitting semiconductor source mounted in the cavity and configured to emit first radiation which peaks at a first wavelength of 405 nanometers, wherein the first radiation has bactericidal, germicidal, or fungicidal characteristics;
a second light emitting semiconductor source mounted in the cavity and configured to emit second radiation which peaks at a second wavelength of 470 nanometers; and
a wavelength conversion material layer formed on top of the first and second light emitting semiconductor sources, wherein the wavelength conversion material layer is configured to generate white light,
wherein an emission spectrum from the light emitting structure comprises a sum of the first radiation, the second radiation, and the white light, wherein the emission spectrum has a peak at the first wavelength and a peak at the second wavelength, and wherein the emission spectrum is without an emission peak at 450 nanometers,
the method comprising:
determining that a surface or object requires disinfection, and
using the light emitting structure to provide the emission spectrum to the surface or object to illuminate and disinfect the exposed surface or object.

2. The method of claim 1, wherein the wavelength conversion material layer is configured to allow at least 10% of the first radiation to be transmitted through the wavelength conversion material layer.

3. The method of claim 1, wherein the wavelength conversion material layer is configured to be bleached by the first radiation.

4. The method of claim 1, wherein the first radiation peak comprises a full width half maximum of below 30 nanometers.

5. The method of claim 1, wherein the light emitting structure further comprises an electrical circuit layer for connecting the first and second light emitting semiconductor sources to an electrical control interface.

6. The method of claim 5, wherein the electrical circuit layer is formed on a top of the substrate.

7. The method of claim 5, wherein the electrical control interface comprises three wires.

8. The method of claim 5, wherein each of the first and second light emitting semiconductor sources are independently controlled at the electrical control interface.

9. The method of claim 1, wherein a Color Rendering Index of a visible part of the emission spectrum is over 70 and a color temperature is between 2000 K and 8000 K.

10. The method of claim 1, wherein at least 5% optical power is emitted between 365 and 430 nanometers.

11. The method of claim 1, where a transmission of the first radiation through the wavelength conversion material layer is between 17 to 24 mW, while a total optical output is between 116 to 126 mW.

12. The method of claim 1, wherein the first light emitting semiconductor source comprises a GaN semiconductor chip.

13. The method of claim 1, wherein the emission spectrum comprises a white light peak in the wavelength range of 470 to 750 nanometers.

14. The method of claim 13, wherein the peak of the white light comprises a full width half maximum of at least 50 nanometers.

* * * * *